US012551624B2

(12) United States Patent
Schader et al.

(10) Patent No.: US 12,551,624 B2
(45) Date of Patent: Feb. 17, 2026

(54) DRUG DELIVERY DEVICE AND METHOD FOR ASSEMBLING

(71) Applicant: Sanofi, Paris (FR)

(72) Inventors: Marc Schader, Frankfurt am Main (DE); William Timmis, Cambridgeshire (GB); Tomas Correa, Cambridgeshire (GB); Andrew Labat-Rochecouste, Cambridgeshire (GB)

(73) Assignee: Sanofi, Paris (FR)

( * ) Notice: Subject to any disclaimer, the term of this patent is extended or adjusted under 35 U.S.C. 154(b) by 851 days.

(21) Appl. No.: 17/598,471

(22) PCT Filed: Mar. 26, 2020

(86) PCT No.: PCT/EP2020/058503
§ 371 (c)(1),
(2) Date: Sep. 27, 2021

(87) PCT Pub. No.: WO2020/200995
PCT Pub. Date: Oct. 8, 2020

(65) Prior Publication Data
US 2022/0184313 A1 Jun. 16, 2022

(30) Foreign Application Priority Data
Mar. 29, 2019 (EP) ..................................... 19305414

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31578* (2013.01); *A61M 5/3202* (2013.01); *A61M 2005/2013* (2013.01); *A61M 2207/00* (2013.01)

(58) Field of Classification Search
CPC .............. A61M 5/3243; A61M 5/3245; A61M 5/3271; A61M 2005/2103;
(Continued)

(56) References Cited

U.S. PATENT DOCUMENTS

| | | | | |
|---|---|---|---|---|
| 2002/0045864 A1* | 4/2002 | Perez | .................. | A61M 5/3271 604/198 |
| 2011/0172602 A1* | 7/2011 | Eaton | .................. | A61M 5/3243 604/134 |

(Continued)

FOREIGN PATENT DOCUMENTS

| | | |
|---|---|---|
| CN | 105517600 A | 4/2016 |
| CN | 108025148 A | 5/2018 |

(Continued)

OTHER PUBLICATIONS

International Preliminary Report on Patentability in International Application No. PCT/EP2020/058503, dated Sep. 28, 2021, 9 pages.

(Continued)

*Primary Examiner* — Emily L Schmidt
*Assistant Examiner* — Samuel J Marrison
(74) *Attorney, Agent, or Firm* — Fish & Richardson P.C.

(57) ABSTRACT

The disclosure relates to a drug delivery device comprising a body extending along a longitudinal axis, at least one arm member arranged within the body and extending essentially parallel to the longitudinal axis, and a container retaining a drug, wherein the container comprises a flange that is arranged at an axial position along the longitudinal axis, wherein the flange has at least one first radial edge region having a first radial distance to the longitudinal axis and at least one second radial edge region having a second radial distance to the longitudinal axis, wherein the second radial distance is greater than the first radial distance, and wherein, (Continued)

in the axial position, the at least one arm member is arranged and configured such that at least one aligning feature of the arm member is arranged at a third radial distance to the longitudinal axis that is smaller than the second radial distance.

31 Claims, 2 Drawing Sheets

(58) Field of Classification Search
CPC ........ A61M 2005/2013; A61M 5/3137; A61M 2005/3139; A61M 2005/208; A61M 5/326; A61M 2005/3264; A61M 2005/3267
See application file for complete search history.

(56) References Cited

U.S. PATENT DOCUMENTS

| | | | | |
|---|---|---|---|---|
| 2012/0053528 | A1* | 3/2012 | Bollenbach | A61M 5/24 29/428 |
| 2012/0323186 | A1 | 12/2012 | Karlsen et al. | |
| 2013/0131602 | A1 | 5/2013 | Kemp et al. | |
| 2013/0289490 | A1 | 10/2013 | Kemp et al. | |
| 2014/0163526 | A1 | 6/2014 | Cabiri et al. | |
| 2016/0354556 | A1* | 12/2016 | Zucker | A61M 5/326 |
| 2017/0312438 | A1 | 11/2017 | Marsh et al. | |
| 2017/0354791 | A1* | 12/2017 | Lewkonya | A61M 5/3129 |
| 2019/0046728 | A1* | 2/2019 | Swanson | A61M 5/2033 |
| 2019/0046737 | A1 | 2/2019 | Glover et al. | |
| 2019/0060579 | A1* | 2/2019 | Daniel | A61M 5/20 |
| 2019/0290859 | A1 | 9/2019 | Helmer | |

FOREIGN PATENT DOCUMENTS

| | | | |
|---|---|---|---|
| CN | 109475699 | A | 3/2019 |
| JP | 2007-505677 | A | 3/2007 |
| JP | 2015-505513 | A | 2/2015 |
| JP | 2016-527036 | A | 9/2016 |
| WO | WO 2005/025636 | A2 | 3/2005 |
| WO | WO 2012/000873 | A1 | 1/2012 |
| WO | WO 2013/119591 | A1 | 8/2013 |
| WO | WO 2015/018578 | A1 | 2/2015 |
| WO | WO 2017/118661 | A1 | 7/2017 |
| WO | WO 2017/144211 | | 8/2017 |

OTHER PUBLICATIONS

International Search Report and Written Opinion in International Application No. PCT/EP2020/058503, dated Jul. 7, 2020, 11 pages.

* cited by examiner

DRUG DELIVERY DEVICE AND METHOD FOR ASSEMBLING

CROSS REFERENCE TO RELATED APPLICATIONS

The present application is the national stage entry of International Patent Application No. PCT/EP2020/058503, filed on Mar. 26, 2020, and claims priority to Application No. EP 19305414.5, filed on Mar. 29, 2019, the disclosures of which are incorporated herein by reference.

TECHNICAL FIELD

The disclosure relates to a drug delivery device. Furthermore, a method for assembling a drug delivery device is disclosed.

SUMMARY

It is an object of the disclosure to provide a drug delivery device, especially a drug delivery device that operates safely and guarantees a use that does not jeopardize the health of patients. Furthermore, a corresponding method for assembling shall be disclosed.

This object may be achieved by the drug delivery device according to claim 1 and by the method according to the independent claim. Further advantageous embodiments are given in the dependent claims.

In one aspect the drug delivery device comprises:

- an preferably elongated body extending along a longitudinal axis,
- at least one arm member arranged within the body and extending essentially parallel to the longitudinal axis, and
- a container for retaining a drug or comprising a drug,
- wherein the container comprises a flange which or which center is arranged at an axial position along the longitudinal axis,
- wherein the flange has at least one first radial edge region having a first radial distance to the longitudinal axis and at least one second radial edge region having a second radial distance to the longitudinal axis,
- wherein the second radial distance is greater than the first radial distance,
- wherein, in the axial position, the at least one arm member is arranged and configured such that at least one aligning feature of the arm member is arranged at a third radial distance to the longitudinal axis that is preferably greater than the first radial distance and smaller than the second radial distance, and
- wherein the arm member and/or the body comprises at least one protruding supporting feature that is arranged and configured to limit a radial movement, e.g. a radial outward movement, of the at least one arm member towards the body in the axial position.

The longitudinal axis may go through the center of the flange and or through the center of a hole within the flange. The body may be essentially cylindrical and the longitudinal axis may correspond to the axis of the cylinder that may be thought as the axis around which a line is rotated to generate the cylinder. Reference may be made to a cylindrical coordinate system, i.e. each position may be defined by three coordinates: axial value (height, distance to zero plane), radial distance to axis and angle between current radial position and a plane that is defined as having angle zero. In this document the words "in an axial position" may mean having an axial coordinate. It depends on the context what value the other coordinates have, i.e. radial and angular coordinate.

It depends on the specific context what the values of the other coordinates are, i.e. angle, radial position The at least one arm member, for instance two arm members or more than two arm members, may be made as thin as possible, for instance to allow short cooling times during molding, i.e. before ejecting the at least one arm member out of a mold part. Short cooling times allow a high throughput during production. The at least one thin arm member may deflect outwardly if there is an axial pressure on it, for instance during the activation of the drug delivery device. The body may limit this outwardly directed deflection. However, there may be a gap between the body and the arm member to allow axial movement of both parts relative to each other. The gap and the flexibility of the arm member may have disadvantages in very special configurations of the drug delivery device. Tolerances for the production of the different pieces may also have to be considered, i.e. for the body, for the arm member and also for the container that comprises the drug. There may be worst case configurations that result for instance into a rotation of the container. This rotation of the container may be transferred to a flange of the container forming a lever that pushes to the arm member. The resulting pressure may result in the outward bending of the arm member into the gap between body and arm member. This bending may lead to a further rotation of the container that is detrimental and that may result in a blockade of relevant functions of the drug delivery device in a worst case.

The proposed construction of the drug delivery device is based on the knowledge that thin arm members may be maintained and an outward deflection may nevertheless be prevented if a supporting protrusion or a protruding supporting feature is used in the critical area only. The protruding supporting feature may limit the movement of the arm member into an outward direction. Protrusions of the protruding supporting feature may be arranged onto the body and/or onto the arm member. The protruding supporting feature may be arranged axially at the axial position of the flange or axially close to the axial position of the flange. "Close" may comprise the range of 0 mm to 10 mm (millimeter) or of 0 to 5 mm or of 0 to 2 mm in proximal direction or in distal direction. The protruding supporting features may only be arranged in these range but not outside of it, for instance if the flange is in a relative position with regard to the at least one arm member that is relevant for an operation state of the drug delivery device. The usage of the proposed protruding supporting feature may result for instance into a safe function of the drug delivery device. It is for instance possible to make sure that a needle cover shield covers the needle after the use of the drug delivery in a sufficient length in order to prevent the user of the drug delivering device from hurting himself or herself or another person after the use of the drug delivery device.

The at least one arm member may be arranged between the body and the container. The flange and the arm member may overlap axially. The container may be arranged within a container holding member. The container holding member may have a non-circular cross section in at least a portion. Thus, there may be two flat lateral surfaces arranged between two curved lateral surfaces. The flange of the container may have the same shape. Thus, the arm member may be supported from all lateral sides by the body and the container holding member within a first portion. The container or a needle on the container may be arranged within a passage that is formed by an arm member support that may for instance connect two arm members. The container may be a syringe that comprises a needle integrally. Alternatively, the container may be a cartridge into which a needle may be inserted prior to use.

The arm member(s) may have several functions, for instance they may be used to trigger a trigger mechanism. The arm member may be moved axially and proximally to trigger the trigger mechanism. While this axial movement is carried out the arm member may act against the force of an energy storing member, for instance a mechanical spring.

The flange of the container may comprise at least one flat portion formed by a lateral flat surface, preferably two flat surfaces that may be arranged in parallel to each other and that are connected by two curved surfaces. This non rotation symmetric flange may have several advantages. Thus, it is not possible that the container rolls due to gravity if it lies on a plane surface that is declined by an angle, for instance on a table. Furthermore, the flats on the flange may allow for a device design that has a smaller diameter compared with a device design for containers that have a flange without a flat. The flange may be used to fix the container against an axial and distal movement when the drug is delivered, for instance using a piston rod that moves axially and distally and that impacts a strong force to the container.

The at least one arm member may extend essentially parallel to the longitudinal axis from a member portion to the proximal end of the drug delivery device. The proximal end may be an end that is opposite the end that is used for injection.

The bending of the at least one arm member may be caused by a rotation of the flange and by the abutment of the flat to an aligning feature of the arm member. The aligning feature may be an aligning edge and/or an aligning surface. The protruding supporting feature may be arranged within the same cross section as the flange. Alternatively, the protruding supporting feature may be arranged close to this cross section, for instance closer than for instance 5 millimeters (mm). Adequate support may, nevertheless, be possible because a flexible arm member may also be rigid within this short distance.

The resulting maximal rotation angle of the flange may be smaller than 2 degrees or smaller than 1 degree. The maximal rotation angle of the flange may be greater than 0.01 degree.

The term "essentially" parallel may comprise a parallel arrangement and slight deviations therefrom, for instance within the tolerances of production, i.e. molding for instance. The deviation may be smaller than an angle of 1 degree, The at least one protruding supporting feature may protrude radially outward from the arm member. Thus, the protruding supporting feature may thereby protrude into a direction into which a force is directed that has to be compensated in order to prevent the bending of the arm member. The distance or value by which the protruding supporting feature protrudes over a surrounding surface of the protruding supporting feature may be in a range of 0.1 millimeter (mm) to 0.3 mm or in a range of 0.15 mm to 0.25 mm, for instance the distance may be 0.2 mm. This distance may correspond to the height of the protruding supporting feature. A gap between body and arm member may be slightly greater, for instance in the range of 0.3 mm to 0.5 mm. These may allow to have a significant effect of the protruding supporting feature. Furthermore, the protruding supporting feature protrudes not too much thereby preventing disadvantages that may arise if these ranges are not used.

It may be easier to arrange the protruding supporting feature on the outside of the arm member than on the inside of the body, for instance with regard to the production of a mold that may be used to produce the pieces of the drug delivery device by injection molding.

Alternatively, the at least one protruding supporting feature may protrude radially inwardly from the body. Thus, the protruding supporting feature may thereby protrude against a direction into which a force is directed that has to be compensated in order to prevent the bending of the arm member. The distance or value of protrusion, for instance the height of the protruding supporting feature, may be in a range of 0.1 millimeter (mm) to 0.3 mm or in a range of 0.15 mm to 0.25 mm, for instance the distance may be 0.2 mm. The gap between the body and the arm member may be for instance in the range of 0.3 mm to 0.5 mm. Protrusion heights within these ranges may not disturb the function of the drug delivery device and may still have a significant effect for the prevention of the bending of the arm member.

The at least one protruding supporting feature may comprise two supporting members or at least three supporting members. The two supporting members or the at least three supporting members may have the same axial distance, for instance relative to a proximal end of the arm member. The two supporting members or the at least three supporting members may preferably comprise ribs or studs. The ribs may extend along a circular curve that has its center of curvature on the longitudinal axis. Alternatively, the ribs may extend along a straight line, especially along a short straight line. The ribs or studs may be shorter than 2 mm, for instance measured circumferentially. The ribs or studs may be longer than 0.5 mm for instance. It may be sufficient to use two comparably short ribs (web) or studs that may be arranged radially outward from the aligning feature that is carried by the arm member. The lengths of the rib may be more than 1.5 or twice the maximal width of the rib. The length of the rib may be shorter than 20 times the maximum width of the rib. The stud may have a width that is equal to the length. However, the width of the stud may be less than 10 percent shorter than its length. Studs with a circular, quadratic, rectangular or elliptical cross section may also be used.

The arm member may comprise at least one inner guide rib that extends parallel to the longitudinal axis and that carries the at least one aligning feature. The aligning feature may comprise an aligning edge that is arranged on the at least one inner guide rib. The at least one inner guide rib of the arm member may extend radially inward from the arm member relative to the longitudinal axis. A height of the at least one inner guide rib may be within the range of 0.5 mm to 1 mm. The at least one inner guide rib may be arranged at a distance to an adjacent long edge of the arm member. The distance between the edge and the inner guide rib may be in the range of 0.5 to 2 mm. The length of the at least one inner guide rib may be at least 2 centimeters (cm). The inner guide rib may not only carry the alignment feature but may also be used to prevent a rotation of the flange if the container is assembled into the drug delivery device. Preferably two inner guiding ribs may be used at one of the at least one arm members.

The arm member may comprise at least one inner local rib that extends parallel to the longitudinal axis and that may carry the at least one aligning feature. The aligning feature may comprise a plane aligning surface that is arranged on the at least one inner local rib. The at least one inner local rib of the arm member may extend radially inward from the arm member relative to the longitudinal axis. The at least one inner local rib may be arranged adjacent to an edge of the arm member, for instance with no offset or distance to the edge. The length of the at least one inner local rib may be at most 1.5 cm (centimeter) or at most 7 millimeters. The at least one inner local rib may comprise a chamfer. The chamfer may be used as a ramp during priming of the drug delivery device, i.e. during the preparation of the drug delivery device for drug delivery. Chamfers may be used on both sides of the local rib or of each local rib. Air bubbles within the drug may be removed for instance during priming by advancing a piston rod of the drug delivery device into an end of the container that is closed by a movable stopper element. One of the at least one arm member may comprise at least two inner local ribs. A height of the at least one inner local rib may be within a range of 0.5 mm to 1 mm. The at least one inner local rib may be arranged with no distance to an adjacent edge of the arm member.

The protruding supporting feature may be rigidly connected to the at least one arm member. There may be material of the arm member within two continuous regions that extend from the protruding supporting feature in the direction of at least two sides that are opposite to each other relative to the protruding supporting feature. The continuous regions may extend from the protruding supporting feature to one long side surface respectively and/or to the ends of the arm member. There may be further continuous regions. Thus the protruding supporting feature may be surrounded on all of its sides by material of the arm member. Spoken with other words, there may be no recesses or apertures going through the arm member close to the protruding supporting feature, especially no recess that is on three sides of the protruding supporting feature and that would add resiliency.

The arm member may be connected to an annularly or cylindrically formed arm member support surrounding a passage that extends along the longitudinal axis. In this case, the at least one arm member and the arm member support may form a needle cover in combination with trigger arms for a trigger mechanism. The resulting needle cover shield member may be formed integrally, for instance during one single injection molding step. Such a needle cover shield member may be part of a drug delivery device that comprises less than ten plastic parts or less than 8 plastic parts. The device may be easy to assemble and it may be a low cost device.

The length of the arm member may be at least equal to the angular width or at least twice, triple or fourfold the angular width of the arm member wherein the angular width is measured in or at the axial position. The arm member may be flexible because of its length. This means that radially outward bending may be an issue that has to be prevented by the protruding supporting feature. "Angular" may refer to an angle that has its vertex on the longitudinal axis and which arms direct radially outward relative to the longitudinal axis.

The at least one arm member may be a first arm member. The drug delivery device may comprise a second arm member arranged within the body and extending essentially parallel to the longitudinal axis. The second arm member may comprise protruding supporting features which are configured in the same way as the protruding supporting features of the first arm member. "Essentially parallel" may comprise parallel and slight variations therefrom, for instance within the tolerances of production, i.e. molding for instance. Two arm members may be used in order to transfer a pressure force via both arm members to two sides of trigger mechanism. The trigger mechanism may comprise an element that is arranged along the longitudinal axis of the body and that comprises protrusions that protrude outwardly and extend to the end portions of the two arm members. These end portions may be proximal end portions. The trigger mechanism may be reliable because two arms are used for triggering. Two or more arm members may be connected by the arm member support mentioned above.

The at least one arm member may be connected to a trigger mechanism that is coupled to an energy storage element for providing a force for expelling the drug. The energy storage element may be a mechanical spring, a high pressure reservoir, etc. Thus, the arm member may be a multi-functional member: aligning the flange and/or preventing rotation of the flange and/or transferring a trigger force to the trigger mechanism. This multi-function may make the drug delivery device simple. The energy storage element may be arranged within the trigger mechanism.

The axial position may be a first axial position on which the flange is arranged in a first state. The first state may be a state in which the drug delivery device is in a pre-use condition and/or wherein it is ready to use. It may be important to make sure that the flange is aligned properly in the first state by using the proposed protruding supporting feature.

The drug delivery device may be configured to be in a pre-assembled state in which the flange of the container is in a proximal axial position that is different from the first axial position, for instance more proximal than the first axial position. The at least one protruding supporting feature may be a first protruding supporting feature. The arm member and/or the body may comprise at least one proximal protruding supporting feature that is arranged and configured to limit radial outward movement of the arm member in the proximal axial position. The proximal protruding supporting feature may be configured in the same way as the first protruding supporting feature and/or have the same or similar function. The proximal axial position may be offset in the proximal direction relative to the arm member and relative to the first axial position.

However, there may be further positions that may have corresponding protruding supporting features: for instance a second position that may be more distal from the first position for the first state. The second position may correspond to a position of the flange in which a second state is reached, for instance a state in which the injection of the drug is triggered by the trigger mechanism and/or in which the injection is started and/or performed. There may be at least one second protruding supporting feature that is arranged in the second position and that may have the same features as the first protruding supporting feature.

A third relevant state may be reached after delivery of the drug into the body of a person. A third axial position may be the position in which the flange of the container is in the third state. The third position may be between the first axial position and the proximal axial position. In this case a needle cover would extend more over the body in the third state compared to the first state. This may allow to show marks or a marked region that indicates to the user that the device has already been used. There may be at least one third protruding supporting feature that is in the third axial position and that may have protruding supporting features that are configured in the same way as the first protruding supporting feature and/or have same or similar functions. However, a first protruding feature and a proximal protruding feature may be sufficient in order to define a range within which outward bending of the arm member may be prevented.

The drug delivery device may be configured such that the at least one arm member moves axially relative to the body if and/or when the drug delivery device is used, especially in order to insert a needle into a patient's body and/or to expel the drug into the body of a patient. This axial movement may allow the construction of a simple device and/or of a device that is simple to use. The drug delivery device may be an auto injector. Alternatively, other arrangements are possible as well. Thus, alternatively, the container may be moved relative to the body in order to insert the needle.

The drug delivery device may comprise a holding member for the container. The holding member may be arranged within the body. The container may be arranged rotatable relative to the holding member. However, this rotation may be limited by the proposed alignment feature and/or by the proposed protruding supporting features. The holding member may further comprise an end portion that has a cross section having a shape that is adapted to the shape of the flange. The holding member may ease the assembling of the drug delivery device considerably, especially if a holding member is used that is inserted into the body together with the container that comprises the drug. An end portion of the container holding member may have at least one third radial edge region having a third radial distance and at least one fourth radial edge region having a forth radial distance that is greater than the third radial distance. The third radial distance may be the same as the first radial distance or there may be a difference between both distances (first and third) that is smaller than 1 mm or smaller than 0.5 mm but greater than for instance 0.01 mm. The fourth radial distance may be the same as the second radial distance or there may be a difference between both distances (second and fourth) that is smaller than 1 mm or smaller than 0.5 mm but greater than for instance 0.01 mm. A middle portion of the holding member may have a more circular cross section than the end portion. Flat surfaces of the end portion of the holding member may be adjacent and/or in direct physical contact with the at least one arm member or with both arm members. This may prevent an inward movement of the arm members if and/or when the arm members are used to activate a trigger mechanism, especially by an axial movement of the arm members against the force of an energy storing member.

The at least one arm member may have a smooth surface in a portion in which the at least one protruding supporting feature is arranged and wherein the at least one protruding supporting feature protrudes from the smooth surface. Thus, the protruding supporting feature may be the only protruding element that extends radially outward in the axial position.

Alternatively, the at least one arm member may have a structured surface in a portion in which the at least one protruding supporting feature is arranged. The at least one protruding feature may protrude from an outer enveloping surface of the structured surface. The structured surface may comprise at least one longitudinal notch/rib or a plurality of longitudinal notches and/or ribs. The purpose of these notches/ribs may be to increase the rigidity of the arm member. The maximal depth of the longitudinal notches/ribs may be smaller than 0.5 mm or smaller than 0.25 mm but greater than 0.01 mm or 10 micrometers. The same may hold for the height of the ribs.

A second aspect relates to a method for assembling a drug delivery device, preferably a drug delivery device according to one of the preceding claims, comprising:

providing a preferably elongated body extending along a longitudinal axis, inserting at least one arm member into the body, preferably from a distal side of the body, inserting a container for retaining a drug and/or comprising a drug into the body through an opening, preferably from a proximal side of the body, wherein the container comprises a flange which or which center is arranged at a proximal axial position along the longitudinal axis, wherein the flange has at least one first radial edge region having a first radial distance to the longitudinal axis and at least one second radial edge region having a second radial distance to the longitudinal axis, wherein the second radial distance is greater than the first radial distance, wherein, in the axial position, the at least one arm member is arranged and configured such that at least one aligning feature of the arm member is arranged at a third radial distance that is preferably greater than the first radial distance and smaller than the second radial distance, and wherein the at least one arm member and/or the body comprises at least one protruding supporting feature that is arranged and configured to limit radial movement, e.g. radial outward movement, of the at least one arm member towards the body in the proximal axial position.

The container may be inserted by gravity, i.e. by letting the container drop or fall into the body through the opening. The fall of the container may be stopped by grabber portions of an inner needle shield that is removed by the grabber portions together with a distal cap of the drug delivery device prior to use. The grabber portion may be made preferably of metal.

There may be cases in which the grabber portions are not completely in their target position and/or do not have a target angle with regard to the longitudinal axis. Each grabber element may have a slightly different position and/or angle with regard to the other grabber elements of the same grabber.

The method may further comprise:

moving the container further away from the opening to a first axial position thereby bringing the flange in a first axial position in which the container is arranged relative to the arm member in the assembled drug delivery device, i.e. in which the container is positioned in the drug delivery device that is ready for use, wherein preferably the at least one arm member and/or the body may comprise at least one first protruding supporting feature that is arranged and configured to limit radial movement of the at least one arm member towards the body in the first axial position.

A special tool may be used to insert the container further into the drug delivery device. The container and/or the flange may have the tendency to rotate during this further insertion step. However, the first protruding supporting feature may limit a bending of the arm member and may limit and/or prevent thereby the rotation of the flange. Without limiting the scope of protection of the proposed features by theory, it may be possible that the rotation tendency results from an imbalance that is introduced by the grabber portions that are arranged in the cap and along which the inner needle cap moves during the further insertion step. The grabber portions may be in intensive and direct physical contact to the inner needle cap. The grabber portions may have sharp edges that promote rotations. The inner needle shield may be hold onto the container for the drug by force fit. Therefore, the rotation that is induced at the inner needle shield may be absorbed by the force fit, i.e. by a rotation of the needle shield relative to the container, if the protruding supporting feature prevents an outward bending of the arm member and thereby a rotation of the container and its flange. Alternatively, if the force fit of the inner needle shield is strong there may be no rotation even in cases in which there is an imbalance induced by the grabber elements because the protruding supporting feature prevents an outward bending of the arm member and thereby a rotation of the container and its flange. Furthermore, jam of the flange with the arm member may be prevented, especially a blocking of the axial movement of the arm member by the flange after delivery of the drug and before and/or until a needle shield that is connected permanently to the arm members is moved again over the needle.

Thus, the features, advantages and technical effects that are valid for the drug delivery device and its embodiments may also be valid for the method and vice versa.

The making and using of the presently preferred embodiments are discussed in detail below. It should be appreciated, however, that the present disclosure provides many applicable concepts that can be embodied in a wide variety of specific contexts. The specific embodiments discussed are merely illustrative of specific ways to make and use the disclosed concepts, and do not limit the scope of the claims.

Moreover, same reference signs refer to the same technical features if not stated otherwise. As far as "may" is used in this application it means the possibility of doing so as well as the actual technical implementation. The present concepts of the present disclosure will be described with respect to preferred embodiments below in a more specific context namely a drug delivery device, especially an auto injector. The disclosed concepts may also be applied, however, to other situations and/or arrangements as well, especially to drug delivery devices that do not comprise auto injectors.

The foregoing has outlined rather broadly the features and technical advantages of embodiments of the present disclosure. Additional features and advantages of embodiments of the present disclosure will be described hereinafter, e.g. of the subject-matter of dependent claims. It should be appreciated by those skilled in the art that the conception and specific embodiments disclosed may be readily utilized as a basis for modifying or designing other structures or processes for realizing concepts which have the same or similar purposes as the concepts specifically discussed herein. It should also be recognized by those skilled in the art that equivalent constructions do not depart from the spirit and scope of the disclosure, such as defined in the appended claims.

BRIEF DESCRIPTION OF THE FIGURES

For a more complete understanding of the presently disclosed concepts and the advantages thereof, reference is now made to the following description in conjunction with the accompanying drawings. The drawings are not drawn to scale. In the drawings the following is shown in.

DETAILED DESCRIPTION

Figure 1:
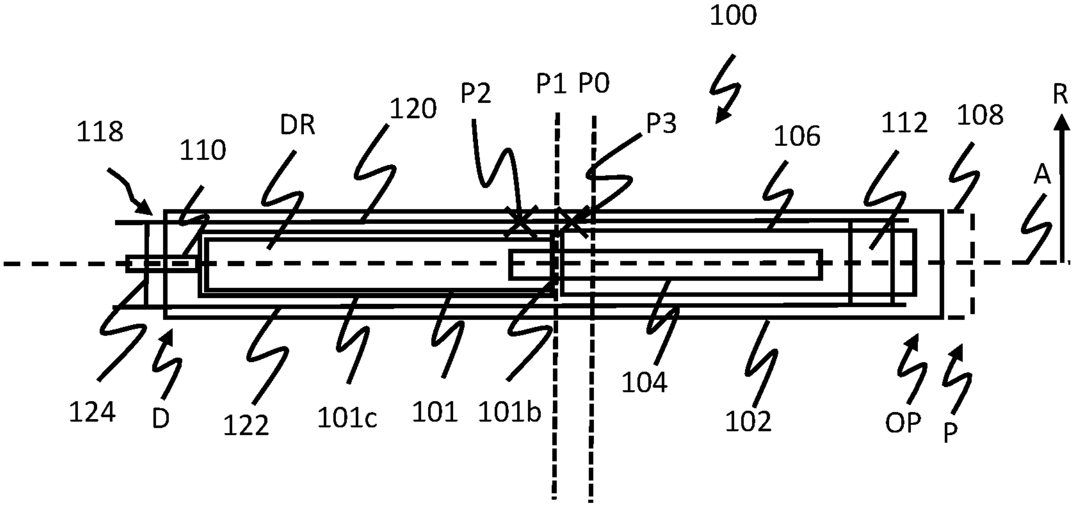
FIG. 1 a drug delivery device.

In this document a proximal end P of a drug delivery device 100 is arranged at an end that faces away from a distal end D of the drug delivery device 100. Distal end D is the end that carries or may carry a needle for injection. FIG. 1 illustrates the drug delivery device 100 that comprises a container holding member 101*c*. The drug delivery device 100 may comprise a main body 102 that houses the container holding member 101*c* completely or partially and that comprises further parts of the drug delivery device 100. The body 102 has a straight longitudinal axis A. A radial direction R is perpendicular (angle of 90 degrees) relative to longitudinal axis A.

Alternatively the main body 102 may be connected to the container holding member 101*c* but may not surround it completely and even may not surround a part of the container holding member 101*c*. Container holding member 101*c* comprises the container 101 that may be inserted into container holding member 101*c*. Container 101 may be made of glass. One end of container 101 may be provided with a small opening and/or a needle 110. The other end of container 101 may comprise a flange 101*b* that may be arranged partially around a second opening of container 101 that may be larger than the small opening.

Within body 102 the following may be arranged:

- a piston rod 104 that is adapted to move a piston/stopper of the container 101 that is within container 101 and that closes the proximal end of container 101,
- a driving mechanism 106 for the piston rod 104. The driving mechanism 106 may comprise an energy storing element, for instance a mechanical spring that is loaded automatically or manually,
- for instance at a proximal end P, an optional actuating element 108 that may be used for the initiation of a movement of the piston rod 104 into the container 101, whereby the driving mechanism 106 is used. A trigger mechanism 112 may be used instead of the actuating element 108 as described below. In this case, a separate proximal cap may be used in order to close a proximal opening OP of body 102.

A drug DR may be dispensed from the container 101 through the needle 110 or through a nozzle that is connectable and/or connected to the distal end D of the drug delivery device 100. The drug delivery device 100 may be a single use device or a multiple use device. The needle 110 may be changed before each use.

The container 101 may be filled with drug DR or medicament. The drug may comprise insulin, hormones, antibodies, or one of the drugs DR listed on the following pages or another drug DR.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or may be used on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, and Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompasses such modifications and any and all equivalents thereof.

Furthermore with regard to FIG. 1, the following may be arranged within body 102:

- a trigger mechanism 112, and
- a flexible needle cover member 118.

Figure 2:
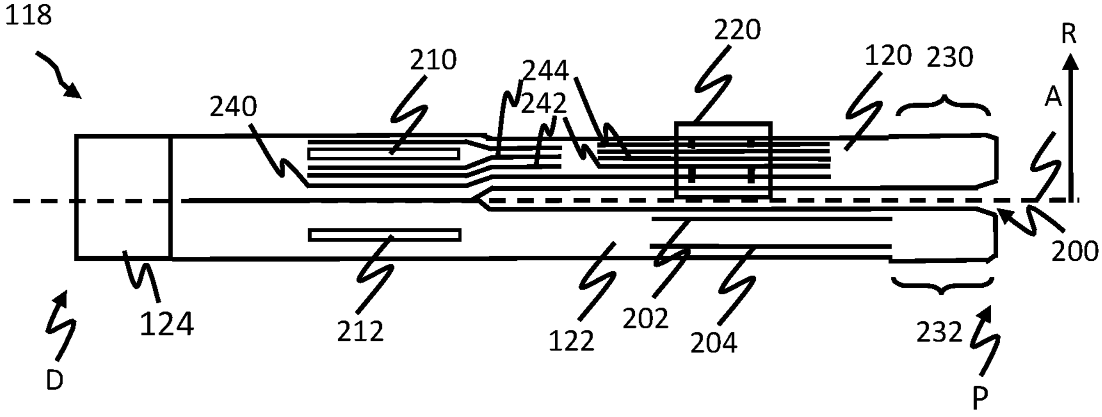
FIG. 2 a needle shield member of the drug delivery device.

Trigger mechanism 112 may be constructed in many ways. Therefore, details of trigger mechanism 112 are not shown in detail. However, one embodiment is described in the following. Trigger mechanism 112 may comprise a trigger part that comprises piston rod 104 that is arranged along longitudinal axis A. The piston rod 104 may comprise two protrusions that extend radially outward into apertures that are formed within the free ends of arms of the needle cover member 118. These free ends are shown in FIG. 2, see reference signs 230 and 232.

Trigger mechanism 112 may be triggered by an axial movement of needle cover member 118 in proximal P direction. A distal end of needle cover member 118 may be pressed against a site of the body of a user of drug delivery device 100. This pressure may result in an axial and proximal movement of needle cover member 118 relative to body 102 and/or relative to container 101 and its flange 101*b*. This axial/proximal movement may be transferred to triggering mechanism 112 against the force of the energy storing member resulting in a triggering of the trigger mechanism 112. This triggering may release the energy storing element. The released energy storing element may push piston rod 104 and a piston/stopper within container 101 into a distal D direction thereby delivering the drug DR through needle 110.

Needle cover member 118 may comprise:

- a first, preferably elongated, arm member 120 and a second, preferably elongated, arm member 122, and
- an arm member support 124.

Arm member support 124 may have a cylindrical shape and may connect both arm members 120, 122. Furthermore, arm member support 124 may comprise a central passage in which needle 110 may be arranged. Arm member 120 and arm member 122 may be arranged with their free ends 230, 232 on or at two sides of trigger mechanism 112 that are opposite to each other. Needle cover member 118 is described with regard to FIG. 2 in more detail below.

FIG. 1 shows several positions P0 to P3 of flange 101*c* relative to needle cover member 118. These positions P0 to P3 may be relevant for different operation states S0 to S3 of drug delivery device:

- position P0: this may be a pre-assembling position in a pre-assembled device state S0 in which container 101 has been inserted loosely into body 102 and in which a distal end of inner needle shield that may cover needle 110 touches grabber elements that may be arranged within an outer cap of drug delivery device 100,
- position P1: this may be a position in a state S1 in which assembling of drug delivery device 100 is finished and in which drug delivery device 100 is ready for use,
- position P2: this may be a position in a state S2 in which trigger mechanism 112 is triggered by needle shield member 118 and in which needle 110 is not covered by needle shield member 118 anymore, i.e. use-condition, and
- position P3: this may be a position in a state S3 in which the drug has been delivered and needle shield member 118 covers the needle 110 again, for instance a little bit more than in state S1.

There may be the following order or sequence of positions P0, P1, P2 and P3 corresponding to greater distances of these positions from proximal end P: position P0, position P3, position P1 and position P2. Position P3 may be the same as position P1 in another embodiment. Alternatively, there may be more or less relevant positions than these four positions P0 to P3.

Assembly of the drug delivery device 100 may be done as stated also in the first half of this documents, i.e.:

providing body 102, inserting needle shield member 118 comprising arm members 120, 122 into body 102, preferably from a distal side D of the body 102, inserting container 101 into the body 102 through opening OP, preferably by gravity, and further inserting container 101, for instance by using a special assembling tool.

Figure 4:
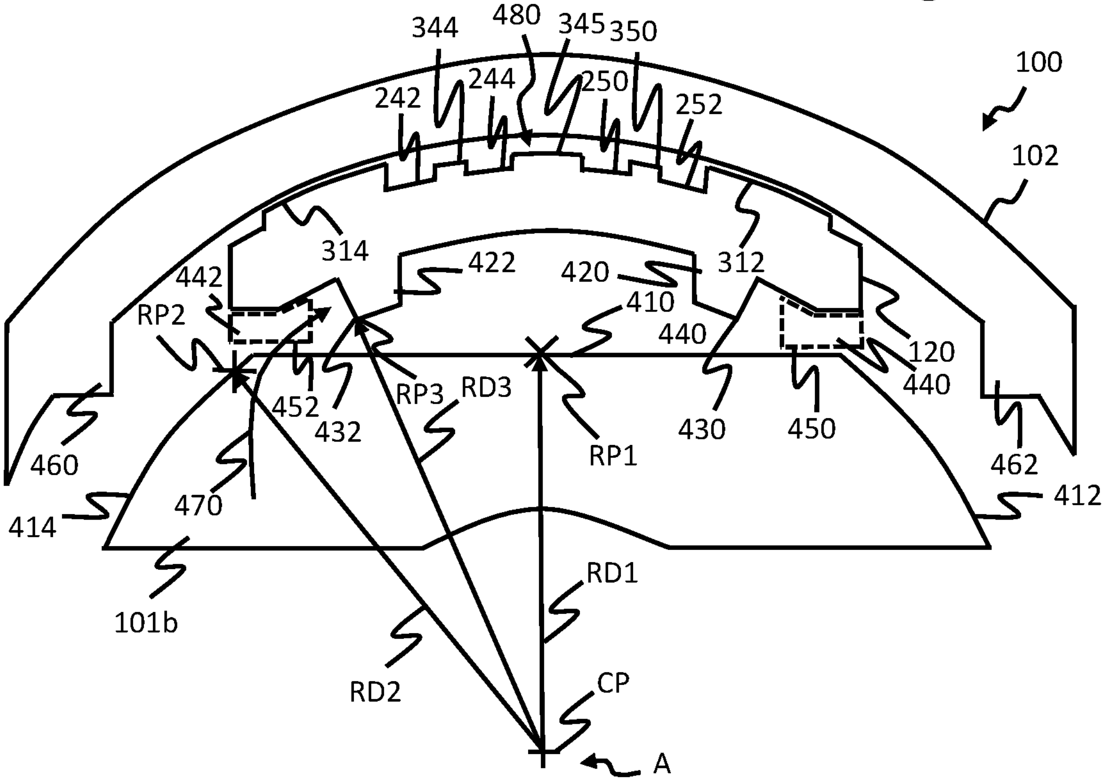
FIG. 4 a cross section through the needle shield member.

FIG. 2 illustrates needle shield member 118 of drug delivery device 100 in more detail. There may be a clearance 200 between the two arm members 120 and 122 of needle shield member 118. FIG. 2 shows the outside of arm member 120 and the inside of arm member 122. Two optional guide ribs 202, 204, i.e. a pair of guide ribs 202, 204, are/is shown on arm member 122. FIG. 4 shows a corresponding pair of optional inner guide ribs 420, 422 on arm member 120. Inner guide ribs 202, 204 may be parallel to each other and may extend parallel to longitudinal axis A. Inner guide ribs 202, 204 may be used to guide flange 101*b* during assembly of drug delivery device 100. Inner guide ribs 202, 204 may further be used to align flange 101*b* after assembly of drug delivery device 100. The length of inner guide ribs 202, 204 may be at least twice the width of the arm member 122 measured in circumferential direction and in the portion that carries inner guide ribs 202, 204.

The clearance 200 may for instance be used as a retaining space for:

container holding member 101*c*, container 101, trigger mechanism 112, piston rod 104, and energy storage member (not shown).

Clearance 200 may allow to see the amount of drug that is in container 101 through one window or through two windows that are arranged in body 102. Optional apertures 210, 212 may be arranged in portions of arm members 120, 122 that are more distal than narrower portions of arm members 120, 122 and that have a greater width than the narrower portions that are arranged more proximally. Apertures 210 and 212 may ease molding of needle shield member 118.

An area 220 on arm member 120 of needle shield member 118 comprises protruding supporting features that are explained in more detail with regard to FIG. 3 below. Arm member 122 comprises features that are configured in the same way compared to protruding supporting features on arm member 120. However, protruding supporting features on arm member 122 are not shown in FIG. 2 because they are arranged on the outside of arm member 122 and only the inside is visible.

End portion 230 forms the free end of arm member 120. In the same way, end portion 232 forms the free end of arm member 122. End portions 230, 232 may comprise apertures and/or ribs that engage the trigger mechanism 112 and that enable the triggering of the trigger mechanism 112.

Both arm members 120 and 122 may be made more rigid using reinforcement features, for instance ribs and/or notches. In the embodiment, a long notch 240 is shown that extends over more than half of the length of arm member 120. Aperture 210 may be arranged in the middle between the edges of the broader part of arm member 120. There may be two further notches 242 and 244 that are arranged between notch 240 and aperture 210. Notches 242 and 244 may be interrupted by a smooth and/or flat surface area onto which an ejector of the mold ejects needle shield member 118. However, this smooth surface area is optional and notches 242 and 244 may have the same length as notch 240. A rib may be formed between notch 240 and an edge of arm member 120. Further ribs may be formed between notches 240 and 242 as well as between notches 242 and 244. This is better visible in FIGS. 3 and 4. Arm member 122 may carry corresponding notches and ribs. However, these ribs and notches are not visible in the perspective view that is shown in FIG. 2.

There may be more or less notches 240 to 254 on needle shield member 118. Furthermore, the shape and/or dimensions (for instance length, width) and/or direction of extension of notches 240 to 254 may be different, for instance depending on the positions of areas that may be used by ejector elements within a mold that is used to produce needle shield member 118.

Figure 3:
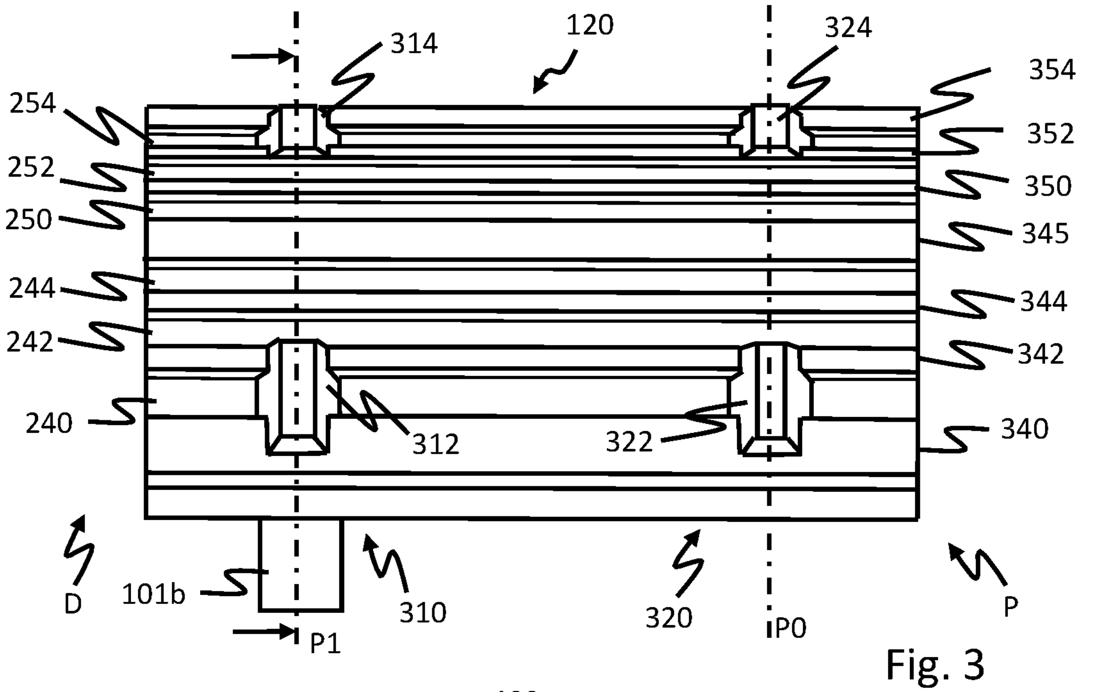
FIG. 3 details of the needle shield member.

FIG. 3 illustrates details of arm member 120 of the needle shield member 118 within area 200 that is shown in FIG. 2. The following notches and ribs are shown from bottom to top: a rib 340, notch 240, a rib 342, notch 242, a rib 344, notch 244, a middle rib 345, a notch 250, a rib 350, a notch 252, a rib 352, a notch 254 and a rib 354 at another long edge of arm member 120. Middle rib 345 may be broader than neighboring ribs 344 and 345. All notches 240 to 254 may have the same depth and the same width. FIG. 3 shows a perspective view in which the real widths of the ribs and notches are distorted. Outer ribs 340 and 354 may also be broader than inner ribs 342, 344, 350 and 352.

A supporting feature 310 is arranged at position P1. Flange 101*b* of the container 100 is arranged at position P1 in the first state of drug delivery device 100. Reference may be made to a proximal end of flange 101*b* or to a point that is arranged in the middle between the distal end of flange 101*b* and the proximal end of flange 101*b* as shown in FIG. 3.

Supporting feature 310 may comprise two supporting members 312, 314. Alternatively, supporting feature 310 may comprise more or less than two supporting members at position P1. The supporting members 312 and 314 may have the form of ribs as shown. Alternatively, other shapes are possible, for instance studs. Supporting member 312 is arranged across notch 240, e.g. perpendicular. Free ends of supporting member 312 are located on rib 340 and on rib 342 which are adjacent to notch 240. Supporting member 314 is arranged across notch 254, e.g. perpendicular. Free ends of supporting member 314 are located on rib 352 and on rib 354 which are adjacent to notch 254. The cross section of supporting members 312 and 314 across its longitudinal axis may be trapezoid, rectangular or may have other appropriate shape. Thus, supporting members 312 and 314 extend circumferential on arm member 120. Supporting members 312 and 314 may not cover other notches 242 to 252 and other ribs 344, 345 and 350.

A further supporting feature 320 is arranged at position P0. Flange 101*b* of container 100 is arranged at position P0 in a pre-assembled state of drug delivery device 100. Reference may be made to a proximal end of flange 101*b* or to a point that is arranged in the middle between the distal end of flange 101*b* and the proximal end of flange 101*b* as may be valid for FIG. 3.

Supporting feature 320 may also comprise two supporting members 322, 324. Alternatively, supporting feature 320 may comprise more or less than two supporting members at position P0. Supporting feature 320 may comprise the same arrangement as supporting feature 310. Alternatively, supporting feature 320 may comprise a different arrangement than the arrangement that is comprised in supporting feature 310. It is possible that supporting feature 320 comprises supporting members that cover different ribs and/or different notches than supporting members 312, 314. Alternatively, the same ribs and/or different notches may be covered as is described in the following. Supporting members 322 and 324 may have the form of ribs as shown. Alternatively, other shapes are possible, for instance studs. Supporting member 322 is arranged across notch 240, e.g. perpendicular. Free ends of supporting member 322 are located on rib 340 and on rib 342 which are adjacent to notch 240. Supporting member 324 is arranged across notch 254, e.g. perpendicular. Free ends of supporting member 324 are located on rib 352 and on rib 354 which are adjacent to notch 240. The cross section of supporting members 322 and 324 across to its longitudinal axis may be trapezoid, rectangular or may have other appropriate shape. Thus, supporting members 322 and 324 extend circumferentially on arm member 120. Supporting members 322 and 324 may not cover other notches 242 to 252 and other ribs 344, 345 and 350.

Thus, supporting features 310 and 320, especially supporting members 312 to 324, are arranged between arm member 120 and an inner side of body 102. In states S0 to S3 in which the flange 101*b* tries to rotate around its own longitudinal axis (may be in the same place as longitudinal axis A) a pressure may be induced radially outward onto arm member 120. However, arm member 120 is supported by supporting members 312 to 324 against the inside of the more stable body 102. Therefore, outward bending of arm member 120 may be prevented by supporting members 312 to 324. Rotation of flange 101*b* may also prevented if arm member 120 does not bend outward. The same is true for arm member 122. This is also visible from a cross section across drug delivery device 100 along the line at position P1 of FIG. 3. This cross section is shown in FIG. 4.

FIG. 4 illustrates a cross section along the line at position P1 shown in FIG. 3. The cross section is through body 102, needle shield member 120 and flange 101*b*. Only the upper half of the cross section is shown. The lower half of the cross section is mirror symmetrical to the upper half and does not show further information. Therefore, the lower half of the cross section is omitted.

A center point CP of the cross section is arranged on longitudinal axis A. The cross section that is shown in FIG. 4 may have an axial position of zero. Thus, all parts or portions of parts within this cross section may have the same axial position, for instance zero millimeter (mm). Positive values for axial positions may be counted in the direction that points out of the plane that comprises the cross section shown in FIG. 4. Negative values for axial positions that are beyond the cross section shown in FIG. 4.

As can be seen in FIG. 4, body 102 may be circularly curved. Body 102 may be cylindrical, i.e. the casing that is formed by body 102 extends along one cycle in the circumferential direction. Arm member 120 may also be circularly curved but has a smaller radius of curvature compared to the radius of curvature of body 102. Arm member 120 extends only along a part of one cycle in circumferential direction, for instance along a part that is less than one quarter or one fifth of a cycle in circumferential direction.

Flange 101*b* may comprise a flat radial edge portion 410 in the upper half and a further flat radial edge portion in the lower half that is not shown. Flange 101*b* may comprise a curved radial edge portion 412 on the right side shown in FIG. 4. A curved radial edge portion 414 of flange 101*b* is shown on the left side of FIG. 4. It may be said that the curved radial edge portions 412, 414 of flange 101*b* are arranged between the flat radial edge portions 410 and/or that the curved radial edge portions 412, 414 connect the flat radial edge portions 410.

Guide ribs 420, 422 may be arranged on the inner side of arm member 120. An aligning feature 430 may be formed by the outer concave edge of rib 420. A further aligning feature 432 may be formed by the outer concave edge of rib 422. Guide ribs 420, 422 may have the same shape and/or length and/or direction of extension and/or functions as guide ribs 202 and 204, see FIG. 2. Aligning feature 430 may stop a rotation of flange 101*b* in a counter clockwise direction, see rotation arrow 470. Aligning feature 432 may stop a rotation of flange 101*b* in a counter clockwise direction. Further aligning features may be arranged on inner guide ribs 202 and 204 of arm member 122.

The following radial positions RP1 to RP3 measured from a center point CP on longitudinal axis A may be relevant for the operation of drug delivery device 100:

- radial position RP1 on flat radial edge portion 410, more specifically in the middle of flat radial edge portion 410, i.e. smallest diameter and smallest radius of flange 101*b*,
- radial position RP2 on curved radial edge portion 414, i.e. greatest diameter and greatest radius of flange 101*b*, and
- radial position RP3 on aligning edge 430 of aligning feature 432 on inner guide rib 422.

All radial positions RP1 to RP3 are located within the plane of the cross section that is shown in FIG. 4. However, the distances between body 102 and arm member 120 and/or between arm member 120 and flange 101*b* are not drawn to scale but shall show the main issues clearly.

Radial position RP1 has a radial distance RD1 from center point CP. Radial position RP2 has a radial distance RD2 from center point CP. Furthermore, radial position RP3 has a radial distance RD3 from center point CP, i.e. from longitudinal axis A in a direction that is directed radially outward. The following relations may be valid in order to enable an appropriate alignment of flange 101*b:*

- radial distance RD1 may be smaller than radial distance RD3, and
- radial distance RD3 may be smaller than radial distance RD2.

Preferably the difference between radial distances RD2 and RD3 should be as small as possible, for instance in the range of 0.01 millimeter to 0.25 millimeter.

FIG. 4 shows clearly a possible arrangement of the inner guide ribs 420 and 422 relative to supporting members 312 and 314 that may have the shape of ribs. Thus, supporting member 312 is arranged radially outward from inner guide ribs 420 and also from alignment feature 430. Therefore, supporting member 312 may prevent outward bending of arm member 120 very efficient if flange 101*b* abuts alignment feature 430. In the same manner, supporting member 314 is arranged radially outward from inner guide rib 422 and also from alignment feature 432. Therefore, supporting member 314 may also prevent outward bending of arm member 120 very efficiently if flange 101*b* abuts alignment feature 432.

Furthermore, FIG. 4 shows the arrangement of notches 242, 244, 250 and 252 as well as of ribs 344, 345 and 350 without the distortions that are due to the perspective of the view in FIGS. 2 and 3.

Ribs 460, 462 may be arranged on the inside of body 102 for guiding and holding container holding member 101*c* that holds container 101 within body 102. Ribs 460 and 462 may extend parallel to longitudinal axis A along at least half of the length of body 102, especially within the proximal half of body 102. Ribs that are similar to ribs 460, 462 may also be arranged within the lower half of the cross section of drug delivery device 100.

In a further embodiment, local ribs 440, 442 may be used instead or in addition to inner guide ribs 420, 422. Local ribs 440, 442 may extend only close to the cross section that is shown in FIG. 4. The length of local rib 440 may be smaller than 5 millimeters or smaller than 3 millimeters. The same length may be valid for local rib 442. Local ribs 440, 442 may comprise aligning features 450, 452 respectively. Aligning feature 450 (452) may be formed by a flat or plane surface. Flange 101*b* abuts against aligning feature 452 if it rotates clockwise, see rotation arrow 470. Flange 101*b* abuts against aligning feature 450 if it rotates counter clockwise. A chamfer may be arranged on one of or on each inner local rib 442 in order to ease priming of drug delivery device 100. The chamfer may act as a ramp during priming. Chamfers may be used on both sides of the local rib 440 or 442 or of each local rib 440, 442.

In a further embodiment, ribs or other protruding supporting features that extend from the inside of body 102 may be arranged in a gap 480 that is between body 102 and arm member 120. There may be a similar gap between body 102 and arm member 122 within the cross section that is shown in FIG. 4. Further body protruding features may be arranged in this similar gap. These ribs or other protruding supporting features may be formed in addition to supporting members 312, 314 or instead of these supporting members 312, 314.

Spoken with other words, bracing and/or supporting ribs on arm members 120, 122 of a needle cover 118 of drug delivery device 100, for instance an auto injector, are disclosed in order to maintain syringe and/or container 101 alignment during assembly and use.

Bracing and/or supporting ribs and other rotation preventing features that are listed below may be used to improve the safety of drug delivery device 100, for instance an autoinjector, and to facilitate a more efficient assembly process, for instance because of the following:

- protecting against a failure of the needle cover 118 to re-extend immediately after post-use, specifically by the added friction caused by a rotated "cut"-type syringe flange or container flange 101*b*,
- removing the requirement for the assembly equipment to maintain rotational alignment during syringe or container 101 insertion.

A "cut"-type syringe flange or container flange 101*b* may be used in drug delivery device 100, for instance in an autoinjector, with a needle cover 118 (shroud) containing long "leg" or "arm" features or arm members 120, 122 that fit tightly around the "cut" area to keep the overall drug delivery device 100 compact. If the syringe or container 101 is rotated, either during assembly or use the rounded part of the flange 101*b* would push into the needle cover arm members 120, 122 squeezing them out into a "bowed" shape. If the flange 101*b* rotates enough it may jam into the bowed arms or arm members 120, 122 and fail to re-extend after use. This would lead to a failure of the drug delivery device 100 to be needle-safe.

Bracing or supporting ribs (supporting members 312 to 324) may for instance extend from the outside of the needle cover arm members 120, 122 to the inside of the outer case or body 102 to prevent the arm members 120, 122 from bowing outwards. This substantially reduces the risk of the syringe or container flange 101*b* being able to rotate far enough such as to become jammed. This has the consequence of improving the safety of post-use of the drug delivery device 100.

This feature enables the assembly equipment involved in inserting the syringe or container 101 to be less complex and less expensive as there is no longer a need to maintain the syringe's or container's 100 rotational alignment through the insertion stroke/assembly stroke.

The concept may for instance consist of small circumferential ribs or other supporting members 312 to 324 extending outwards from the arms of the needle cover 118. Their function may be to prevent the "bowing" or the outward deflection or bending of the arms 120, 122 if and when the syringe or container flange 101*b* rotates into guide ribs 420, 422 which may be located on the inside of each arm member 120, 122.

Axially, the circumferential ribs or other supporting members 312 to 324 may be located at least at the final position of the syringe flange or container flange 101*b* during assembly and potentially further back, e.g. more proximally P, to protect against "bowing" during the assembly stroke.

The position of the bracing/supporting ribs or of other supporting members 312 to 324 relative to the syringe or container flange 101*b*, the bulk of the needle cover arm members 120, 122 geometry and the outer case or outer body 102 of the drug delivery device 100 may be as is shown in FIGS. 1 to 4.

The following solutions may be considered and applied individually or in any arbitrary combination:

1. Height of Inner Guide Ribs 420, 422 on Needle Cover Member 118

A clearance between the ribs 420, 422 and the surfaces of syringe or container flange 101*b* may be preferred but only "just". Inner guide ribs 420, 422 on needle cover 118 may have sufficient height.

Parts affected: needle cover member 118 (metal off change, i.e. metal has to be removed if the mold is already produced).

Solution robustness: depending on rib height that has been selected there may be still a clearance between the inner guide rib 420, 422 and the syringe or container flange 101*b* at worst case, i.e. when using comparably high but cost effective tolerances of mold and/or molded parts. There may be a comparably high interference between these both parts at 4.5 sigma.

Risks: moldability: low, function: low, assembly: low.

2. Ribs or Protrusions on the Inside of the Body 102

May prevent arm members 120, 122 from bowing outwards.

Parts affected: body 102 (metal off change), may involve considerable tool rework if the mold already exists.

Solution robustness: depending on rib height that has been selected, there may still be a clearance between the inner guide rib 420, 422 and the syringe or container flange 101*b* at worst case, i.e. when using comparably high but cost effective tolerances of mold and/or molded parts. There may be a comparably high interference between these both parts at 4.5 sigma.

Risks: moldability: would require tooling from both ends, function: low, assembly: medium.

Ribs or protrusions on the inside of the body 102 may for instance be arranged within gap 480 in addition or instead of supporting members 312, 314.

3. Brace or Support the Back of the Needle Cover Arm Member 120, 122 with Outer Ribs or Protrusions on the Outside of the Needle Cover Member 118, See FIGS. 1 to 4

May prevent arm members 120, 122 from bowing outwards.

Parts affected: needle cover member 118 (metal off change)

Solution robustness: depending on rib height of supporting members 312 to 324 that has been selected, there may still be a clearance between the inner guide rib 420, 422 and the syringe or container flange 101*b* at worst case, i.e. when using comparably high but cost effective tolerances of mold and/or molded parts. There may be a comparably high interference between these both parts at 4.5 sigma.

Risks: moldability: low, function: low, assembly: medium.

4. Combination of Solutions 1 and 3

Inner guide ribs 420, 422/protrusions on needle cover member 118 with sufficient height and bracing/supporting of the back of the needle cover arm member 120, 122 with outer ribs/protrusions (supporting members 312 to 324) on needle cover 118. This may be a preferred solution.

Parts affected: needle cover member 118 (metal off change).

Solution robustness: medium. Depending on rib/protrusion height that has been selected, there may be an interference between the inner guide rib 420, 422/protrusion and the syringe or container flange 101*b* at worst case, i.e. when using comparably high but cost effective tolerances of mold and/or molded parts. Interference between these both parts at 4.5 sigma may be higher than in solution 3.

Risks: moldability: low, function: low, assembly: medium.

5. New Ribs 440, 442 on Needle Cover Member 118 Outboard of Existing Ribs 422 or Instead of Existing Ribs 422

Local to the region around the final position of the syringe or container flange 101*b* (so as to avoid changes of the drive spring holder guidance features), and optionally with a chamfer on inner local ribs 440, 442 acting as a ramp during priming. Chamfers may be used on both sides of the local rib 440, 442 or of each local rib 440, 442.

This solution could be coupled with bracing/supporting features to prevent arm members 120, 121 bowing outwards.

Parts affected: needle cover (metal-off change, adds additional undercuts), syringe/container holding member 101*c* (metal-on change, i.e. metal has to be added if the mold already exists, welding is one possibility to add metal)

Solution robustness: medium-high

These features act on the most effective part of the syringe/container flange 101*b* to prevent or undo rotation.

Risks:

moldability: medium, function: high; new part interaction added, and assembly: high.

The intention of the bracing/supporting ribs and of the other solutions may be to prevent any rotation of the container 101, e.g. PFS (pre filled syringe), at the point when a rigid needle shield (RNS) or the inner needle shield hits grabber prongs meaning that no clearance should be available between aligning feature, for instance 432, and flange 101*b*. The rigid needle shield may form an inner cover of needle 110. The grabber prongs may be comprised within a distal cap or distal outer cover that protects also the rigid needle shield.

Although embodiments of the present disclosure and their advantages have been described in detail, it should be understood that various changes, substitutions and alterations can be made therein without departing from the spirit and scope of the disclosure as defined by the appended claims. For example, it will be readily understood by those skilled in the art that many of the features, functions, processes and methods described herein may be varied while remaining within the scope of the present disclosure. Moreover, the scope of the present application is not intended to be limited to the particular embodiments of the system, process, manufacture, method or steps described in the present disclosure. As one of ordinary skill in the art will readily appreciate from the disclosure of the present disclosure systems, processes, manufacture, methods or steps presently existing or to be developed later that perform substantially the same function or achieve substantially the same result as the corresponding embodiments described herein may be utilized according to the present disclosure. Accordingly, the appended claims are intended to include within their scope such systems, processes, methods or steps. Further, it is possible to combine embodiments mentioned in the first part of the description with examples of the second part of the description which relates to FIGS. 1 to 4.

LIST OF REFERENCE SIGNS

A longitudinal axis
D distal end
P proximal end
R radial direction
OP opening
DR drug
100 drug delivery device
101 container
101*b* flange
101*c* container holding member
102 body (main housing part)
104 piston rod
106 driving mechanism
108 optional actuating element
110 needle
112 trigger mechanism
118 flexible needle cover member
120, 122 arm member
124 arm member support
P0 to P3 position
200 clearance
202, 204 inner guide ribs
210, 212 aperture
220 area
230, 232 end portion
240 to 244 notch
250 to 254 notch
310 supporting feature
312, 314 supporting member
320 supporting feature
322, 324 supporting member
340 to 345 rib
350 to 354 rib
RP1 to RP3 radial position
RD1 to RD3 radial distance
410 flat radial edge portion
412, 414 curved radial edge portion
420, 422 guide rib
430, 432 aligning feature
440, 442 local rib
450, 452 aligning feature
460, 462 rib for holding member
470 rotation arrow
480 gap

The invention claimed is:

1. A drug delivery device comprising:

a body extending along a longitudinal axis;

at least one arm member arranged within the body and extending essentially parallel to the longitudinal axis; and a container for retaining a drug, wherein the container comprises a flange that is arranged in an axial position along the longitudinal axis, wherein the flange has at least one first outer radial edge region having a first radial distance to the longitudinal axis and at least one second outer radial edge region having a second radial distance to the longitudinal axis, wherein the second radial distance is greater than the first radial distance, wherein the at least one arm member is arranged and configured such that at least one aligning feature of the at least one arm member is arranged in the axial position at a third radial distance to the longitudinal axis that is smaller than the second radial distance, wherein the at least one arm member and/or the body comprises at least one protruding supporting feature that is arranged in the axial position and configured to limit a radial movement of the at least one arm member towards the body in the axial position, wherein the drug delivery device is configured such that the at least one arm member moves axially into the body of the drug delivery device when an arm member support is pressed against a site on a body of a user of the drug delivery device, and wherein the at least one arm member is configured to activate a trigger mechanism of the drug delivery device by transferring a trigger force to the trigger mechanism via an axial movement of the at least one arm member.

2. The drug delivery device according to claim 1, wherein the at least one protruding supporting feature protrudes radially outwardly from the at least one arm member.

3. The drug delivery device according to claim 2, wherein the at least one protruding supporting feature protrudes radially outwardly from the at least one arm member by a distance that is in a range of 0.1 mm to 0.3 mm or in a range of 0.15 mm to 0.25 mm.

4. The drug delivery device according to claim 1, wherein the at least one protruding supporting feature is arranged on the body and protrudes radially inwardly from the body.

5. The drug delivery device according to claim 4, wherein the at least one protruding supporting feature protrudes radially inwardly from the body by a distance that is in a range of 0.1 mm to 0.3 mm or in a range of 0.15 mm to 0.25 mm.

6. The drug delivery device according to claim 1, wherein the at least one protruding supporting feature comprises at least two supporting members.

7. The drug delivery device according to claim 1, wherein the at least one arm member comprises at least one inner guide rib that extends parallel to the longitudinal axis and that carries the at least one aligning feature, and wherein the at least one inner guide rib of the at least one arm member extends radially inwards from the at least arm member relative to the longitudinal axis.

8. The drug delivery device according to claim 1, wherein the at least one arm member comprises at least one inner local rib that extends parallel to the longitudinal axis and that carries the at least one aligning feature, wherein the at least one inner local rib of the at least one arm member extends radially inwards from the at least one arm member relative to the longitudinal axis, and wherein the at least one inner local rib is arranged adjacent to an edge of the at least one arm member.

9. The drug delivery device according to claim 1, wherein the at least one protruding supporting feature is rigidly connected to the at least one arm member.

10. The drug delivery device according to claim 1, wherein the at least one arm member and the arm member support are part of a single molded piece, and wherein the arm member support annularly or cylindrically surrounds a passage that extends along the longitudinal axis.

11. The drug delivery device according to claim 1, wherein a length of the at least one arm member is at least equal to an angular width or at least twice, triple, or fourfold the angular width of the at least one arm member, wherein the angular width is measured in the axial position.

12. The drug delivery device according to claim 1, wherein the at least one arm member is a first arm member, wherein the drug delivery device comprises a second arm member arranged within the body and extending essentially parallel to the longitudinal axis, wherein the second arm member comprises protruding supporting features that are configured in the same way as the protruding supporting features of the first arm member, and wherein the at least two arm members are mirrored symmetrically with regard to each other at the axial position.

13. The drug delivery device according to claim 1, wherein the axial position is a first axial position on which the flange is arranged in a first state, and wherein the first state is a state in which the drug delivery device is in a pre-use condition, and/or wherein the drug delivery device is ready to use.

14. The drug delivery device according to claim 13, wherein the drug delivery device is configured to be in a pre-assembled state in which the flange of the container is in a proximal axial position that is different from the first axial position, wherein the at least one protruding supporting feature is a first protruding supporting feature, wherein at least one proximal protruding supporting feature is arranged on the at least one arm member in the proximal axial position and configured to limit radial movement of the at least one arm member towards the body in the proximal axial position, and wherein the proximal protruding supporting feature protrudes radially outward.

15. The drug delivery device according to claim 1, wherein the at least one protruding supporting feature comprises a stud or a rib arranged on the axial position.

16. The drug delivery device according to claim 15, wherein the rib comprises a circumferential rib.

17. The drug delivery device according to claim 1, wherein the drug delivery device is configured such that the at least one arm member moves axially relative to the body if the drug delivery device is used.

18. The drug delivery device according to claim 1, wherein the trigger mechanism is coupled to an energy storage element for providing a force for expelling the drug.

19. The drug delivery device according to claim 1, wherein the drug delivery device comprises a holding member for the container; wherein the holding member is arranged to be within the body; and wherein the container is arranged rotatable relative to the holding member.

20. The drug delivery device according to claim 1, wherein the at least one arm member has a smooth surface in a portion in which the at least one protruding supporting feature is arranged and wherein the at least one protruding supporting feature protrudes from the smooth surface.

21. The drug delivery device according to claim 1, wherein the at least one arm member has a structured surface in a portion in which the at least one protruding supporting feature is arranged and wherein the at least one protruding supporting feature protrudes radially outward from an outer surface of the structured surface.

22. The drug delivery device according to claim 21, wherein the structured surface comprises at least one longitudinal notch and at least two longitudinal ribs.

23. The drug delivery device according to claim 22, wherein the at least one protruding supporting feature extends circumferentially and covers the at least one notch.

24. The drug delivery device according to claim 23, wherein a length of the at least one protruding supporting feature is smaller than the length of the at least two longitudinal ribs.

25. The drug delivery device according to claim 1, wherein the at least one protruding supporting feature comprises at least two supporting members, which are arranged on the same arm member of the at least one arm member in the axial position and at two different circumferential positions.

26. The drug delivery device according to claim 1, wherein the aligning feature is configured to prevent rotation of the flange when the container is assembled into the drug delivery device by providing an edge that limits the rotation of the flange.

27. The drug delivery device according to claim 1, wherein the container retains the drug.

28. A method for assembling a drug delivery device, the method comprising:

providing a body extending along a longitudinal axis;

inserting at least one arm member into the body; and thereafter inserting a container for retaining a drug or comprising the drug into the body through an opening, wherein the container comprises a flange that is arranged in an axial position along the longitudinal axis, wherein the flange has at least one first outer radial edge region having a first radial distance to the longitudinal axis and at least one second outer radial edge region having a second radial distance to the longitudinal axis, wherein the second radial distance is greater than the first radial distance, wherein the at least one arm member is arranged and configured such that at least one aligning feature of the at least one arm member is arranged in the axial position at a third radial distance to the longitudinal axis that is smaller than the second radial distance, wherein the at least one arm member and/or the body comprises at least one protruding supporting feature that is arranged in the axial position and configured to limit radial movement of the at least one arm member towards the body in the axial position, and wherein the drug delivery device is configured such that the at least one arm member moves axially into the body of the drug delivery device when an arm member support is pressed against a site on a body of a user of the drug delivery device.

29. The method according to claim 28, further comprising moving the container further away from the opening to a first axial position in which the container is arranged relative to the arm member in the drug delivery device in an assembled state, wherein the at least one arm member and/or the body comprises at least one first protruding supporting feature that is arranged and configured to limit radial movement of the at least one arm member towards the body in the first axial position.

30. The method according to claim 28, wherein the opening is a proximal opening within the body.

31. A method comprising:

delivering a drug using a drug delivery device, wherein the drug delivery device comprises:

a body extending along a longitudinal axis;

at least one arm member arranged within the body and extending essentially parallel to the longitudinal axis; and a container for retaining the drug, wherein the container comprises a flange that is arranged in an axial position along the longitudinal axis, wherein the flange has at least one first outer radial edge region having a first radial distance to the longitudinal axis and at least one second outer radial edge region having a second radial distance to the longitudinal axis, wherein the second radial distance is greater than the first radial distance, wherein the at least one arm member is arranged and configured such that at least one aligning feature of the at least one arm member is arranged in the axial position at a third radial distance to the longitudinal axis that is smaller than the second radial distance, wherein the at least one arm member and/or the body comprises at least one protruding supporting feature that is arranged in the axial position and configured to limit a radial movement of the at least one arm member towards the body in the axial position, wherein the drug delivery device is configured such that the at least one arm member moves axially into the body of the drug delivery device when an arm member support is pressed against a site on a body of a user of the drug delivery device, and wherein the at least one arm member is configured to activate a trigger mechanism of the drug delivery device by transferring a trigger force to the trigger mechanism via an axial movement of the at least one arm member.

* * * * *